United States Patent [19]

Maeda

[11] Patent Number: 4,828,673
[45] Date of Patent: May 9, 1989

[54] APPARATUS FOR MEASURING COMBUSTIBLE GAS CONCENTRATION IN FLUE GAS

[75] Inventor: Masato Maeda, Tokyo, Japan
[73] Assignee: Yokogawa Electric Corporation, Tokyo, Japan
[21] Appl. No.: 162,717
[22] Filed: Mar. 1, 1988
[30] Foreign Application Priority Data
  Mar. 9, 1987 [JP] Japan .................................. 62-53496
[51] Int. Cl.⁴ ........................................... G01N 27/46
[52] U.S. Cl. .................................... 204/427; 204/421; 204/424
[58] Field of Search ................. 204/1 S, 1 T, 421–429
[56] References Cited
  U.S. PATENT DOCUMENTS
  3,366,554  1/1968  Linblad ............................... 204/1 T
  3,578,578  5/1971  von Krusenstierna ............. 204/426
  3,791,936  2/1974  Pebler et al. ......................... 204/427
  4,049,524  9/1977  Togawa et al. ..................... 204/427

*Primary Examiner*—T. Tung
*Attorney, Agent, or Firm*—Moonray Kojima

[57] ABSTRACT

An apparatus having a combustible gas detecting sensor and an $O_2$ gas detecting sensor which are provided separately of each other, the combustible gas detecting sensor made of zirconia solid electrolyte and having an electrode exposed to reference gas and a molybdenum disilicide electrode exposed to gas to be measured, wherein the combustible gas detecting sensor is heated to an operating temperature which is different from the heating temperature of the $O_2$ detecting sensor, thereby to measure the concentration of a wide range of combustible gas in the gas to be measured which is in an $O_2$ gas rich state, by calculation based on the respective outputs of the two sensors.

3 Claims, 4 Drawing Sheets

APPARATUS FOR MEASURING COMBUSTIBLE GAS CONCENTRATION IN FLUE GAS

BACKGROUND OF THE INVENTION

1. Field of Invention

This invention relates to an apparatus for measuring combustible gas concentration in a flue gas occuring in combustion processes; and more particularly, to such an apparatus which is capable of sensitively measuring the concentration of a very small amount of combustible gas in a flue gas which is in an $O_2$ gas rich state.

2. Discussion of the Prior Art

In a combustion process, it is preferable to monitor at all times the concentrations of $O_2$ and a combustible gas such as CO in the flue gas flowing through a duct or stack and effect combustion control so that the combustion furnace is run in optimal conditions from the viewpoint of conservation of energy and prevention of environmental pollution. In general, the optimal value of $O_2$ is within the range of from 1 to 5%, while the optimal value of CO is within the range of from 150 to 300 ppm. Therefore, the flue gas is in a state wherein $O_2$ gas is rich.

As one example of apparatus for measuring CO gas in the above state, a catalytic combustible sensor is commercially available from AMETEK, Inc and called "WDG-IIIC". In this type of sensor, the flue gas, which is sucked in from the duct or stack through a filter, is guided outside of the duct through a pipe to a sensor section where it is burned catalytically, and the concentration of combustible gas contained in the flue gas is measured on the basis of change in the temperature.

In this type of prior art measuring system, however, the sensor cannot be inserted directly into the duct and hence there is a need for a suction mechanism for guiding the gas outside of the duct through a pipe. Furthermore, the gas to be measured must be supplied to the sensor section at a predetermined flow rate. However, the flow rate of the suction gas may be changed by clogging of the piping outside of the duct, resulting disadvantageously in a zero drift or span drift. The prior art further suffers from the disadvantage that the sensor sensitivity is low at a combustible gas concentration of about 200 ppm which is essential to combustion control.

Another prior art apparatus for measuring CO gas in an $O_2$ rich state comprises an infrared CO meter and is commercially available from Land Combustion, Ltd. In this prior art apparatus, a light emitting section, which emits infrared light that contains a wavelength region that is absorbed by combustible gas, and a light receiving section, which receives the infrared ray which has been subjected to absorption, are provided directly at both sides of the duct to measure the combustible gas concentration. This type of measuring apparatus has the advantage that it is possible to selectively measure the concentration of a desired combustible gas even if a plurality of combustible gases are mixed together and contained in the flue gas. Also, the response is quick as compared with the catalytic combustible sensor. Moreover, the sensitivity is high at the essential combustible gas concentration.

This prior art infrared CO meter has many disadvantages. For example, since this prior art apparatus is an optical system, the mechanism is complicated and the overall size thereof is increased, which results in an increase in the cost. Since this apparatus cannot be installed in a place where the temperature is relatively high, the installation conditions are limited. After the apparatus has been mounted on the wall of a duct, no calibration can be effected using a standard gas. Therefore, the reliability of such prior art apparatus is disadvantageously low.

U.S. Pat. No. 4,231,733 discloses a sensor which is capable of separately measuring the concentration of $O_2$ gas and a combustible gas in a flue gas by use of an oxygen ion conductive solid electrolytic cell. In this sensor, when $O_2$ in the gas which is to be measured is $O_2$ rich, measurement is carried out in a voltage measuring mode to thereby meassure the $O_2$ gas concentration on the basis of the level of the electromotive force which changes in accordance with the oxygen partial pressure difference between the measured gas and a reference gas. When there is very little $O_2$ in the measured gas and/or the combustible gas is rich, the measuring circuit is switched over so as to connect a constant voltage source between two electrodes of the sensor to measure the amount of current flowing in accordance with the amount of oxygen consumed by the combustion reaction of the combustible gas, thereby measuring the combustible gas concentration.

However, the conditions in which the combustible gas can be measured with this system are such that the $O_2$ concentration is 0.01% or less and the combustible gas is rich. On the other hand, in the combustion control the measurement of the combustible gas concentration is carried out with respect to the flue gas which is in a state wherein the concentration is from 1 to 5%, while the amount of CO gas which is to be measured is very small, i.e. from 150 to 300 ppm. Thus, this prior art apparatus cannot be used for such purposes.

Japan Laid Open Patent No. 60-61654 discloses an apparatus which is capable of measuring a very small amount of combustible gas in a flue gas which is in an $O_2$ gas rich state, by the use of a solid electrolytic cell. In this apparatus, a measuring electrode which is contacted by a gas to be measured is provided at one side of a solid electrolyte, while a reference elettrode which is contacted by a reference gas whose oxygen partial pressure is known, is provided at the other side of the solid electrolyte, to thereby constitute a measuring cell. The measuring electrode comprises a first electrode which allows combustion, i.e. catalytic, reaction to proceed until the $O_2$ gas and combustible gas in the gas to be measured reach a chemical equilibrium, and a second electrode having relatively low catalytic activity which prevents the combustion reaction from proceeding until the $O_2$ gas and combustible gas in the gas to be measured reach a chemical equilibrium. Calculation is made on the basis of two different kinds of electro motive forces which are respectively generated between the first and second measuring electrodes and the reference electrode, thereby enabling measurement of the respective rpartial pressures of the combustible gas and the $O_2$ gas in the measured gas. Moreover, this apparatus uses for the second electrode material having relatively low catalytic activity, such as platinum material, such as platinum, platinum-vanadium alloy, or the like, and gold material, such as gold, gold-platinum alloy, or the like.

However, when a platinum material is used for the second electrode, the catalytic power is so high that a very small amount of combustible gas cannot be measured with sensitivity. When a gold material is used, gold diffuses into the solid electrolyte as time passes, thus causing detecting characteristics to become deteriorated.

When the first and second measuring electrodes are heated, they are disposed in an enclosed heating space. The first electrode which has a high catalytic activity causes the combustible gas and $O_2$ gas in the gas to be measured, to react actively with each other, so that the combustible gas is oxidized. Since the gas which is measured can reach the electrode portion only by diffusion, the concentration of the combustible gas around the second electrode changes, and this affects the results of the measurement.

Furthermore, since the first and second electrodes are heated at the same temperature, it is impossible to select an optimal temperature for each of the electrodes. Thus, each electrode is unable to conduct measurement under optimal conditions.

SUMMARY OF THE INVENTION

Accordingly, an object of the invention is to overcome the aforementioned and other deficiencies and defects and disadvantages of the prior art.

Another object is to provide an apparatus which is capable of measuring a wide range of combustible gas from the ppm level in a gas which is in an $O_2$ gas rich state, with a high degree of response and sensitivity.

A further object is to provide an apparatus for measuring the wide range of combustible gas, which has a simplified arrangement, reduced overall size and lowered production costs.

A still further object is to provide an apparatus for measuring the wide range of combustible gas which is not restricted by installation conditions.

The foregoing and other objects and advantages are attained by the invention which encompasses an apparatus for measuring a combustible gas concentration in a flue gas, comprising a combustible gas detecting Zirconia solid electrolytic sensor having one electrode thereof given a reference gas and the other electrode thereof given a gas to be measured, the other electrode being formed from a Molybdenum disilicide layer, and an $O_2$ gas detecting sensor, the sensors being inserted directly into a duct carrying the gas to be measured for concentration in a wide range and which is in an $O_2$ gas rich state by calculation made on the basis of the respective outputs of the combustible gas detecting sensor and the $O_2$ gas detecting sensor.

The $O_2$ gas detecting sensor may comprise a Zirconia oxygen sensor using a platinum electrode. The combustible gas, e.g. CO, in the measured gas catalytically reacts with oxygen to generate an electromotive force corresponding to the partial pressure of oxygen remaining in the gas to be measured. If $O_2$ gas is rich and CO gas is present in a very small amount, there is substantially no difference between the electromotive forces before and after reaction. In the combustible gas sensor, both $O_2$ gas and CO gas in the gas to be measured, reach the Zirconia interfacial portion of the electrode and therefore it is possible to obtain an output corresponding to a composite potential which comprises an electromotive force concerning the oxygen partial pressure and an electromotive force generated through the direct reaction of the combustible gas with $O^{2-}$ ions inside the Zirconia solid electrolyte.

The electromotive force generated from the $O_2$ gas sensor is expressed according to Nernst's equation in the form of an equation which includes the $O_2$ gas concentration and the CO gas concentration in the gas to be measured, as two variables. On the other hand, the electromotive force generated from the combustible gas sensor is expressed by an approximate equation which includes the $O_2$ gas concentration and CO gas concentration in the gas to be measured, as two variables. Thus, the CO concentration in the gas to be measured is obtained by calculation based on the basis of these equations.

DETAILED DESCRIPTION OF PREFERRED EMBODIMENTS

Figure 1:
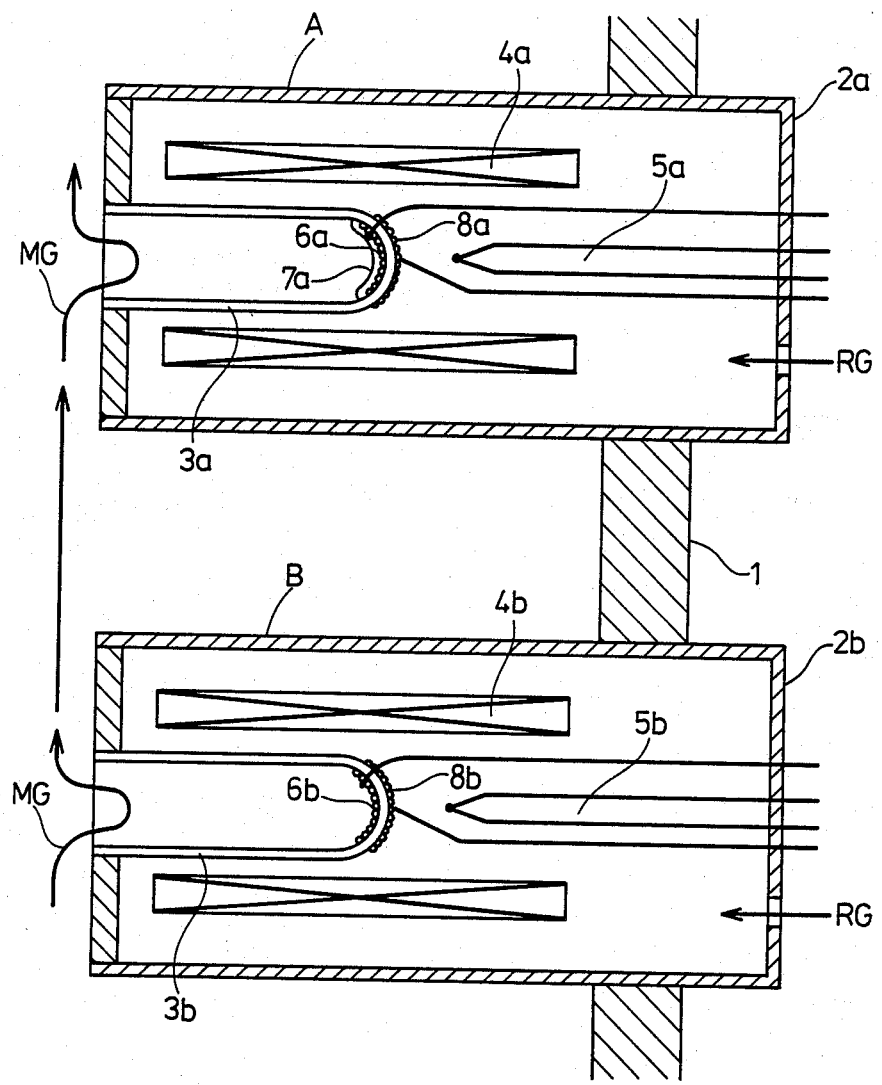
FIG. 1 is a sectional view depicting an illustrative embodiment of the invention.

FIG. 1 depicts a wall 1 of a duct through which flue gas MG flows, and an $O_2$ gas sensor probe A and a combustible gas sensor probe B. The sensor probe A has a casing 2a in which are provided a test tube shaped zirconia solid electrolytic sensor 3a, a heater 4a for heating the sensor 32, and a temperature sensor 5a. Sensor probe B has a casing 2b in which are similarly provided a test tube shaped zirconia sensor 3b, a heater 4b for heating this sensor 3b, and a temperature sensor 5b. In sensor probe A, a platinum catalytic layer 6a, which is an inner electrode, having a strong catalytic power is provided on the inner surface of the zirconia sensor 3a which is contacted by gas MG to be measured. The inner electrode is covered with another catalytic layer 7a. An outer electrode 8a is provided on the outer surface of zirconia sensor 3a which is contacted by a reference gas RG.

Figure 4:
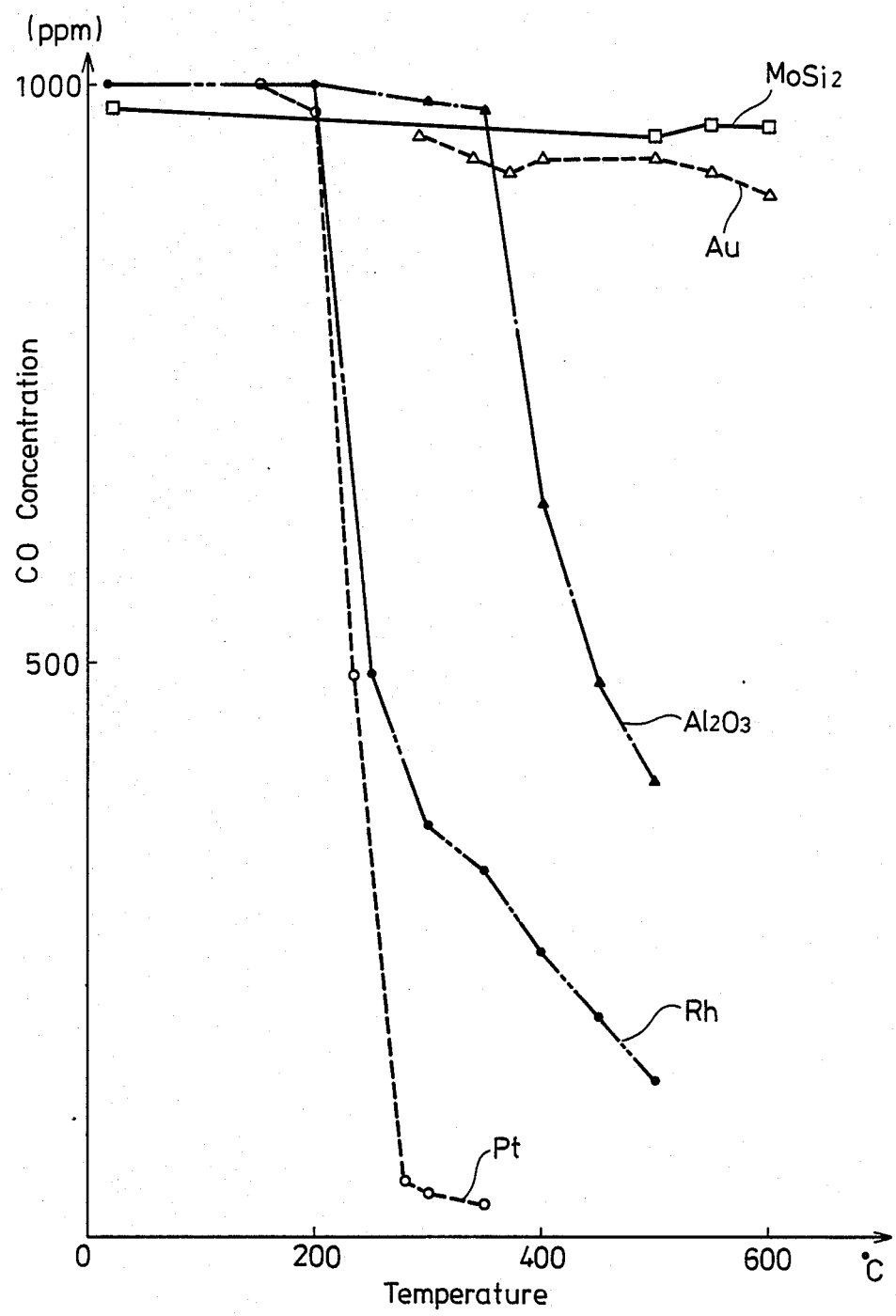
FIG. 4 is a graph depicting the results of experiments carried out on various electrode materials to examiner their catalytic powers.

In sensor probe B, an inner electrode 6b is provided on the inner surface of sensor 3a, which is contacted by gas MG to be measured, electrode 6b being defined by a molybdenum disilicide layer, the catalytic power of which can be ignored. An outer electrode 8b is provided on the outer surface of zirconia sensor 3b which is contacted by reference gas RG. The details of examination made to find an optimal electrode material and eventual selection of molybdenum disilicide electrode film will be explained with reference to FIG. 4.

In the experiment, various kinds of electrode materials were placed in respective quartz test tubes and heated. With the mouth of each test tube covered, a sample gas having a CO concentration of 1000 ppm and an $O_2$ cocentration of 1% were led into the inside of the test tube to carry out catalytic reaction. After completion of the reaction the sample gas was analyzed with an infrared gas analyzer to measure the concentration of CO gas contained in the sample gas. A low CO gas concentration shows that the catalytic reaction has proceeded at the electrode material being tested.

The following were tested: molybdenum disilicide ($MoSi_2$), gold (Au), aluminum oxide ($Al_2O_3$), rhodium (Rh), and platinum (Pt). As will be made clear from FIG. 4, below 200° C. the catalytic power of all materials is so low that it can be ignored. On the other hand, when the temperature exceeds 200° C., the catalytic power of platinum increases suddenly, resulting in lowering of the CO concentration in the sample gas. As the temperature rises further, rhodium and aluminum oxide also increases in terms of catalytic power and show a similar tendency. On the other hand, the catalytic power of molybdenum disilicide and gold is so low that it can be ignored even at 600° C.

On the basis of the experimental results, the inventor further carried out experiments using molybdenum disilicide and gold for inner electrode 6b of sensor probe B. As a result, it was discovered that inner electrode 6b made of gold changes with time and this leads to deterioration of the characteristics. The reason for this may be that gold diffuses inside the zirconia solid electrolyte to form a kind of alloy which impairs the movement of oxygen ions. In the case of molybdenum disilicide, on the other hand, no changes occur with time. Although in the experimental results shown in FIG. 4 molybdenum disilicide exhibits no catalytic power below 600° C., the heating temperature is preferably set so as to be as low as possible within the range in which the function of the zirconia sensor is not lowered, because the place where the sensor probe is actually used is a duct wherein a large amount of dust is present. Thus, the dust accumulated on the electrode portion functions to enhance the catalytic power. On the basis of these experimental results, the inventor selected molybdenum disilicide as a material for the inner electrode 6b of sensor probe B.

The sensor 3a in sensor probe A is heated by heater 4a to a temperature at which sensor 3a becomes an oxygen ion conductor, e.g. 750° C. A combustible gas component, e.g. CO, contained in the measured gas MG causes the following catalytic reaction at platinum catalytic film 7a.

$$CO + (\tfrac{1}{2})O_2 \rightarrow CO_2 \qquad (1)$$

As a result, an electromotive force corresponding to the amount of oxygen remaining unconsumed after this reaction is generated between the electrodes of sensor 3a. If it is assumed that the $O_2$ concentration in the measured gas MG is x%, the CO gas concentration therein is y% and the $O_2$ concentration in the reference gas RG is 20.6%, the electromotive force $E_A$ may be expressed according to Nernst's equation as follows.

$$E_A = k_A \cdot (R \cdot T_A / 4F) \cdot \ln(20.6/(x-(\tfrac{1}{2})y)) + C_A \qquad (2)$$

wherein F is Faraday's constant; R is the gas constant; $T_A$ is the operating temperature; and $k_A$ and $C_A$ are constants.

On the other hand, sensor probe B is heated to a temperature lower than the heating temperature of zirconia sensor 3b, e.g. 550° C. At this temperature, the catalytic power of the molybdenum disilicide electrode is so low that it can be ignored. Thus, both the $O_2$ gas and the CO gas in the measured gas MG, reach inner electrode 6b. Taking into consideration the experimental results, the inventor considered the following approximate equation (4). The $O_2$ gas generates an electromotive force concerning the ratio of the oxygen partial pressure (x%) in the measured gas MG to oxygen partial pressure (20.6%) in the reference gas RG according to Nernst's equation.

On the other hand, the CO gas generates an electromotive force through a direct reaction with $O^{2-}$ ions inside the zirconia solid electrolyte as follows.

$$CO + O^{2-} \rightarrow CO_2 + 2e \qquad (3)$$

The magnitude of the electromotive force thus generated depends on the kind of material for the electrode 6b or the operating temperature, and a voltage which is approximated according to the following equation is obtained between electrodes of the sensor 3b.

$$E_B = (1 + k_B y) \cdot (R \cdot T_B / 4F) \cdot \ln(20.6/x) + C_B \qquad (4)$$

wherein $T_B$ is the operating temperature, and $k_B$ and $C_B$ are constants.

Figure 2:
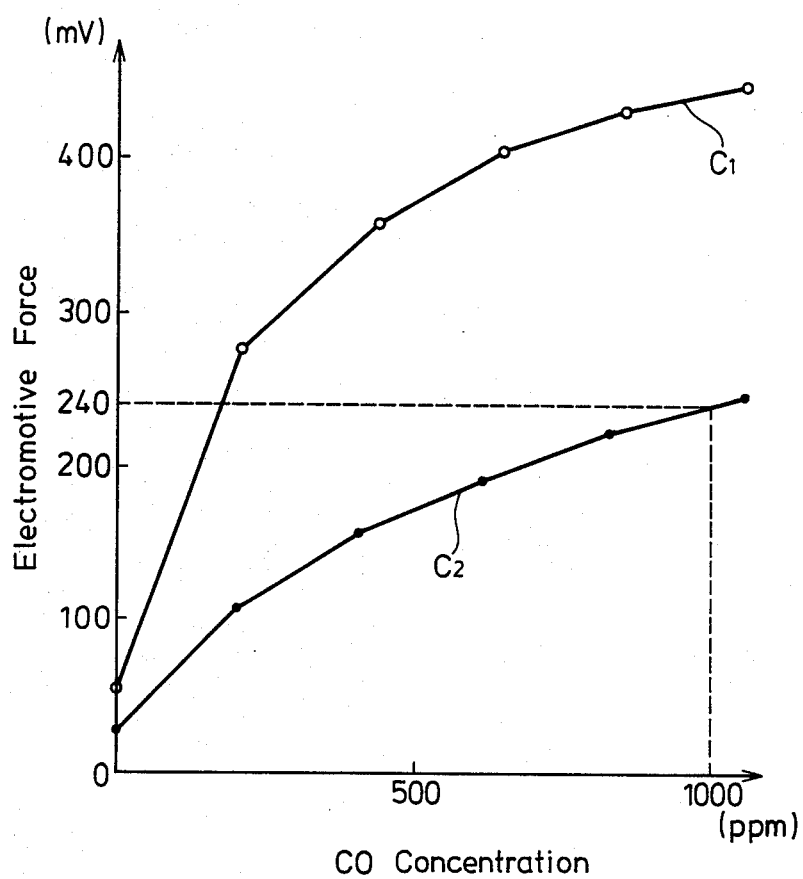
FIGS. 2 and 3 are graphs depicting experimental results of a combustible gas sensor having an inner electrode formed of molybdenum disilicide.

This approximate equation (4) traces the experimental results shown in FIG. 2 with a relatively high degree of accuracy. More specifically, FIG. 2 shows the experimental results obtained when molybdenum disilicide was used for inner electrode 6b. In this experiment, CO gas was added to each of the two kinds of gas having two different $O_2$ concentrations, and experiments were carried out with the CO concentration being variously changed. The temperature was 550° C., which was lower than the operating temperature, i.e. 750° C., of conventional zirconia sensors. $C_1$ and $C_2$ denote characteristic curves obtained from equation (4). Curve $C_1$ represents the characteristics of a mixed gas consisting of a gas having an $O_2$ concentration of 0.4% and CO gas. $C_2$ curve represents the characteristics of a mixed gas consisting of a gas having an $O_2$ concentration of 2.4% and CO gas. These characteristic curves are approximate to the experimental results with a relatively high degree of accuracy. It will be understood from these experimental results that the CO concentration has non-linear characteristics which depend on the $O_2$ concentration.

The inventor further carried out experiments concerning the sensor probe B, and as a result, found that the sensor output characteristics can be approximated with a considerably high degree of accuracy by the following simple equation.

$$E_B' = (K_B' \cdot \ln y) - (h_B \cdot \ln x) + C_B' \qquad (5)$$

wherein $E_B'$ is the electromtive force generated from the zirconia sensor 3b, and $k_B'$, $h_B'$ and $C_B'$ are constants.

Figure 3:
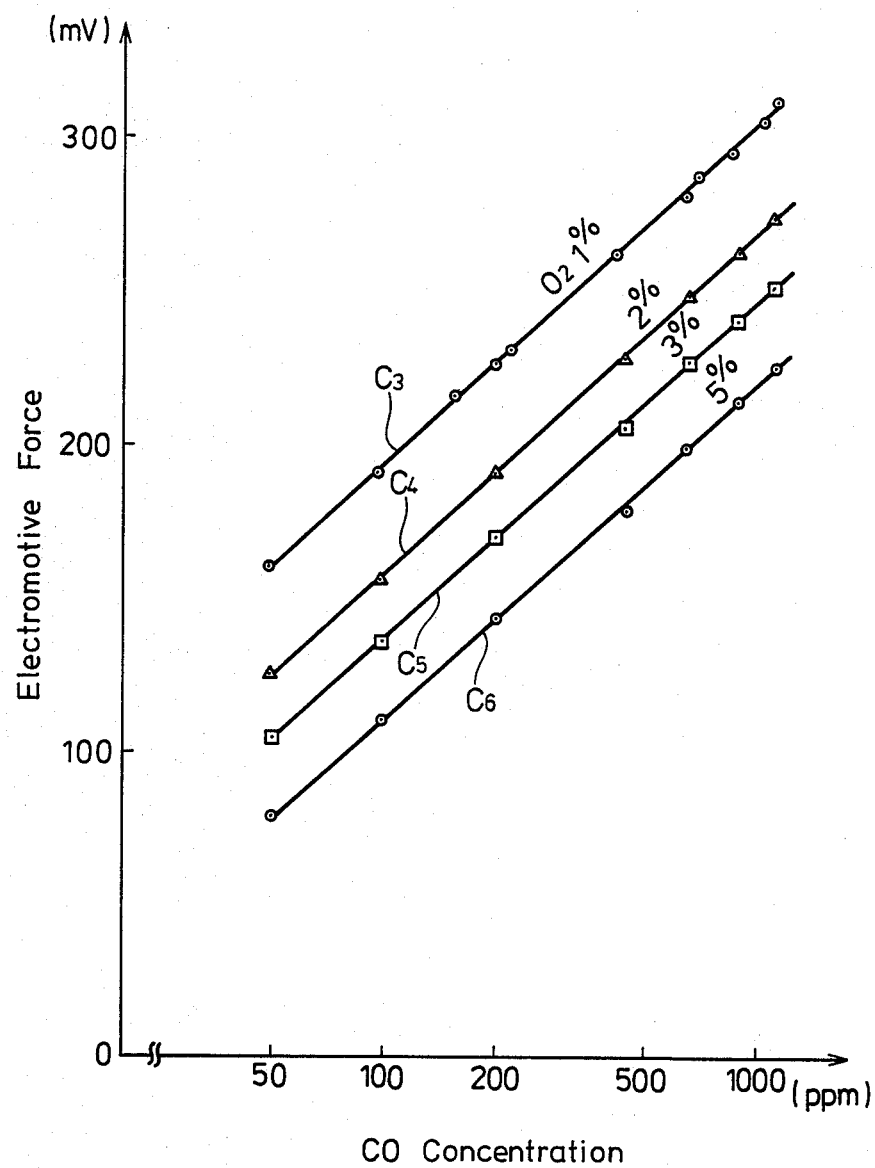

FIG. 3 depicts results of experiments carried out at 500° C. using molybdenum disilicide for inner electrode 6b. In FIG. 3 the axis of abscissas represents the CO concentration on a logarithmic scale. $C_3$ to $C_6$ are characteristic curves obtained from equation (5). Curve $C_3$ represents the characteristics of a mixed gas consisting of a gas having an $O_2$ concentration of 1% and CO gas. Curve $C_4$ represents the characteristics of a mixed gas consisting of a gas having an $O_2$ concentration of 2% and CO gas. Curve $C_5$ represents the characteristics of a mixed gas consisting of a gas having an $O_2$ concentration of 3% and CO gas. Curve $C_6$ represents the characteristics of a mixed gas consisting of a gas having an $O_2$ concentration of 5% and CO gas. The plotted dots show experimental results. The characteristic curves accurately trace the experimental results. The constants $k_A$, $C_A$, $k_B$ and $C_B$ in equations (2) and (4) or constants $k_A$, $C_A$, $k_B'$, $h_B'$ and $C_B'$ in equations (2) and (5) may be obtained using two different kinds of measured gas MG in which the $O_2$ concentration x and the combustible gas concentration y are known. Accordingly, with respect to a measured gas MG in which component concentrations are known, it is possible to obtain the CO gas concentration y in the measured gas, and, at the same time, the $O_2$ concentration x by solving the simultaneous equations (2) and (4) or simultaneous equations (2) and (5).

The invention has the following advantages.

1. It is possible to measure accurately a wide range of amounts of combustible gas in a measured gas which is an $O_2$ gas rich state.

2. Since the combustible gas detecting sensor and the $O_2$ gas detecting sensor are inserted directly into a duct through which a measured gas flows, the apparatus has a simplified arrangement, a reduced size overall and excellent response.

3. With zirconia sensors, if the operating temperature is set at an excessively low level, the function lowers. However, with molybdenum disilicide used for the combustible gas sensor, the operating temperature is relatively high and this sensor is operable at 450° C. to 650° C., although this temperature is lower than that (e.g. 750° C.) of conventional zirconia sensors. In the case of Curve $C_4$, wherein $O_2=2\%$, shown in FIG. 3, it is possible to obtain a sufficiently high electromotive force, e.g. 270 mV, at a CO concentration of 1000 ppm.

4. Since the combustible gas sensor and the $O_2$ gas sensor are provided separately, it is possible to select an optimal heating temperature for each sensor and hence conduct measurements of the two under optimal conditions.

5. The invention sensor can advantageously be used where the temperature is relatively high, and hence the sensor is not restricted by installation conditions.

Although in the foregoing embodiment a zirconia oxygen sensor is used as the $O_2$ gas sensor, the invention is not so limited. Also, although an $O_2$ gas sensor is used to measure the concentration of $O_2$ in the measured gas, if the $O_2$ concentration is known, it is possible to measure the concentration of a combustible gas in the measured gas with the combustible gas sensor alone.

The foregoing description is illustrative of the invention. Numerous modifications and extensions thereof would be apparent to the worker skilled in the art. All such modifications and extensions are to be considered to be within the spirit and scope of the invention.

What is claimed is:

1. An apparatus for measuring a combustible gas concentration in a flue gas comprising a combustible gas detecting zirconia solid electrolytic sensor comprising one electrode to which a reference gas is applied and another electrode to which a gas to be measured is applied, said other electrode being a molybdenum disilicide electrode film, whereby wide concentration of combustible gas in said gas to be measured is measured on the basis of output from said sensor and $O_2$ gas concentration in said gas to be measured.

2. An apparatus for measuring a combustible gas concentration in a flue gas comprising a combustible gas-detecting zirconia solid electrolytic sensor comprising one electrode to which a reference gas is applied and another electrode to which a gas to be measured is applied, said another electrode being molybdenum disilicide electrode film; and an $O_2$ gas detecting sensor, both said sensors being inserted directly into a duct through which said gas to be measured flows, thereby to measure wide concentrations of combustible gas in said gas to be measured which is in an $O_2$ gas rich state by calculation made on the basis of respective outputs of said combustible gas detecting sensor and said $O_2$ gas detecting sensor.

3. An apparatus for measuring a combustible gas concentration in a flue gas comprising a combustible gas detecting zirconia solid electrolytic sensor comprising one electrode to which a reference gas is applied and another electrode to which a gas to be measured is applied, said other electrode being a molybdenum disilicide film; and an $O_2$ gas detecting zirconia solid electrolytic sensor comprising one electrode to which a reference gas is applied and another electrode to which the gas to be measured is applied, the other electrode being of a platinum film, wherein said two sensors being inserted directly into a duct through which said gas to be measured flows, wherein said $O_2$ gas detecting sensor is heated to an operating temperature at which said sensor becomes an oxygen ion conductor, wherein said combustible gas detecting sensor is heated to a lower temperature than said operating temperature, thereby to measure wide concentration of combustible gas in said gas to be measured which is in an $O_2$ gas rich state, by calculation made on the basis of respective outputs from said combustible gas detecting sensor and said $O_2$ detecting sensor.

* * * * *